United States Patent [19]

Sullivan

[11] Patent Number: 5,064,637

[45] Date of Patent: Nov. 12, 1991

[54] SUBSTITUTED SULFONAMIDE DERIVATIVES WHICH INHIBIT ALLERGIC REACTIONS

[75] Inventor: Timothy J. Sullivan, Dallas, Tex.

[73] Assignee: Board of Regents, The University of Texas System

[21] Appl. No.: 358,789

[22] Filed: May 30, 1989

[51] Int. Cl.$^5$ .................. A61K 31/655; A61K 37/02
[52] U.S. Cl. ......................................... 424/9; 514/150;
534/664; 534/774; 534/798
[58] Field of Search .............. 534/774, 798, 664; 514/150

[56] References Cited

U.S. PATENT DOCUMENTS

| | | | |
|---|---|---|---|
| 2,228,303 | 1/1941 | Fischer | 534/774 |
| 2,257,813 | 8/1941 | West et al. | 534/774 X |
| 2,396,145 | 3/1946 | Anders et al. | 534/664 |
| 2,430,439 | 11/1947 | Winnek et al. | 534/798 X |
| 2,665,273 | 1/1954 | Mast et al. | 534/664 |
| 3,053,827 | 9/1962 | Langley | 534/798 |
| 3,144,448 | 8/1964 | Kano et al. | 534/798 X |
| 3,239,506 | 3/1966 | Stanin et al. | 534/798 X |
| 3,681,319 | 8/1972 | Lindberg et al. | 534/664 |
| 3,915,951 | 10/1975 | Agback et al. | 534/664 |
| 4,219,474 | 8/1980 | Zalipsky et al. | 534/664 |
| 4,412,992 | 11/1983 | Chan | 534/664 X |
| 4,479,899 | 10/1984 | Hamprecht | 534/774 X |
| 4,529,589 | 7/1985 | Davydov et al. | 534/798 X |

FOREIGN PATENT DOCUMENTS

| | | | |
|---|---|---|---|
| 222214 | 1/1957 | Australia | 534/798 |
| 458667 | 8/1949 | Canada | 534/798 |
| 1925051 | 11/1970 | Fed. Rep. of Germany | 534/798 |

OTHER PUBLICATIONS de Weck et al. II, Int. Arch. Allergy. 42:782–797 (1972).

Goth, A., Medical Pharmacology, Ninth Edition (1978), pp. 568–573.
Sullivan, J. Allergy Clin. Immunol., vol. 74, (1984) 594–599.
Warrington et al., Clin. Allergy, vol. 13 (1983) 235–240.
Carrington et al., J. Allergy Clin. Immunol., vol. 79 (1987) 442–447.
deWeck et al., Int. Arch. Allergy, vol. 42 (1972) 798–815.
Sullivan et al., International Conference on AIDS, Jun. 4–9, 1983, Montreal, Canada.
Dialog Search Report.
2,703,492 08–1978 W. Germany Takayanagi II 514 150 08.
Poraswamy et al., J. Indian Chem. Soc., vol. 23, pp. 277 to 280 (1946).

*Primary Examiner*—Robert W. Ramsuer
*Attorney, Agent, or Firm*—Arnold, White & Durkee

[57] ABSTRACT

The present invention involves intradermal, percutaneous, parenteral, or enteral administration of a newly synthesized compound to detect, reduce, or eliminate the occurrence of allergic reactions to sulfonamides. The new compound is a substituted sulfonamide, the substituent being bound to the paraamino (4-position) group through an azo, amide, or other linkage. Because a purpose of the substituent is to make the new compound water soluble, it can take a variety of forms, but it must contain carbon and hydrogen, plus at least one of oxygen and nitrogen. Examples of usable substituents include imidazole, a carbohydrate, or an amino acid such as histidine, tyrosine, tryptophan, lysine, or tyrosine methyl ester; it may also be a synthetic polymer, polypeptde, polysaccharide, or an amino acid homopolymer.

27 Claims, No Drawings ns cited.
SUBSTITUTED SULFONAMIDE DERIVATIVES WHICH INHIBIT ALLERGIC REACTIONS

BACKGROUND OF THE INVENTION

Research relating to the present invention was partially supported by grant 000545 from the American Foundation for AIDS Research.

Abbreviations used herein include:
$N^4$-SM: $N^4$-sulfonamidoyl determinant SMX: Sulfamethoxazole SMX-HD: $N^4$-sulfamethoxazoyl-L-histidine SMX-HSA: $N^4$-sulfamethoxazoyl-human serum albumin BSA: Bovine serum albumin SM: Sulfonamide TM: Trimethoprim IH: Immediate hypersensitivity Literature citations in the following descriptions are listed at the end of the specification and are incorporated in pertinent part by reference herein for the reasons cited.

Therapy with SM is accompanied by cutaneous, gastrointestinal, renal, hepatic, or hematologic complications in up to 10% of cases[1-3] despite the recent avoidance of topical administration of SM and the use of lower doses of SM when doses are combined with TM. Many of the adverse reactions to SM are believed to be immunologically mediated.[1-14] Some of the reactions reported have clinical characteristics of anaphylaxis, urticaria, angioedema, serum sickness, contact sensitivity, and photoallergic reactions; each form suggesting that classic immunopathologic mechanisms may have been active.[1-14] Cutaneous eruptions occur in 1% to 2% of patients who receive SM alone and in approximately 6% of patients who receive TM/SM combinations.[2,3] Pruritic rashes typical of IgE-mediated reactions comprise a significant fraction of the adverse reactions to SM. These problems are increasingly important in the context of expanding clinical use of SM, particularly in combination with TM or erythromycin.[9]

The immunochemistry of SM allergy in man is not completely understood. Haptenation of human molecules by SM[10] or metabolism followed by haptenation[5,11] has been suspected for many years but never has been unequivocally proven. Reactivity to the para-aminophenyl substituent, to determinants derived from quinone metabolites, and to the SM substituent have been proposed to explain experimental and clinical observations.[5,10,11] IgE antibodies to SM were documented nearly 40 years ago by Sherman and Cooke[10] in convincing passive transfer experiments, but the determinants recognized by the IgE were not delineated. Studies of human contact sensitivity to SM, as assessed by patch testing[5,11,12] and lymphocyte transformation assays[3,14] have provided insights into the presence and specificity of what appear to be lymphocytemediated reactions. Evidence of immunopathologic reactions to SM abounds, but systematic studies of human immune responses to SM clearly are needed to improve diagnosis and knowledge of the pathophysiology of SM allergy.

Experiments described were designed to explore the possibility that in vivo conjugation of SM via the $N^4$-para-amino group or the adjacent benzyl substituent leads to the formation of immunogenic and pathogenic drugcarrier conjugates. Human IgE to SM was detected by use of SMX linked to cellulose via the $N^4$-amino group. Inhibition studies indicated that at least some of the antibodies bound free, unmodified SM. These experiments suggested that patients who experience immediate hypersensitivity-like reactions to SM often express IgE to an SM determinant that closely resembles the native drug bound to a carrier by some form of linkage through or near the $N^4$-amino group.[15]

The hypothesis has been tested that patients who experience immediate hypersensitivity reactions to sulfonamides (SM) express IgE that can bind to a $N^4$-sulfonamidoyl determinant ($N^4$-SM). Sulfamethoxazole (SMX) was coupled to CNBr-activated cellulose disks to form a matrix predominantly substituted with isourea-linked $N^4$-SMX determinants. After incubation of human sera with these disks or bovine serum albumin substituted disks as a control, the binding of IgE was assessed with $^{125}$I-labeled antihuman IgE. The binding ratios (counts per minute SMX disks per counts per minute bovine serum albumin disks) for sera from nonallergic donors and newborn infants averaged 1.11 ($\pm 0.21$SD). Sera from 10 patients with histories of apparent immediate hypersensitivity reactions to SM were studied. Ratios $\geq 2.1$ ($>4$ SD above control) were detected in 70% (seven of 10). Significant binding was detected in the sera of three of seven patients with other forms of SM allergy. Preincubation with SMX (80 mmol/L) inhibited binding 7% to 35% in eight of the 10 positive sera tested. Binding of one highly reactive serum was significantly inhibited by SMX, sulfamethizole, and sulfamerazine, but not sulfanilic acid or Trimethoprim. The results of this study suggested that $N^4$-SM is a major determinant recognized by IgE to SM and that an in vitro assay capable of detecting IgE to SM has been developed.[15]

SUMMARY OF THE INVENTION

The present invention involves a newly synthesized compound having the formula $R^1$-$N^4$-sulfonamide, wherein $R^1$ is bound to N4 of sulfonamide. $R^1$ comprises carbon, hydrogen and one or more of oxygen and nitrogen. Said $R^1$-$N^4$-sulfonamide is water-soluble. $R^1$ may be an amino acid such as histidine, tyrosine, tryptophan, lysine or tyrosine methyl ester, for example. It is also predicted that their substituents, for example carbohydrates, may be likewise utilized. $R^1$ is preferably bound to the $N^4$ nitrogen of the sulfonamide through an azo linkage, although other types of linkages such as amide bonds may be used.

A preferred sulfonamide drug for the practice of the present invention is sulfamethoxazole. For example, the compounds of the present invention with this drug may be characterized as having the formula: $R^3$-$N^4$-sulfamethoxazole, wherein $R^3$ is bound to $N^4$ of $N^4$-sulfmethoxazole. $R^3$ comprises carbon, hydrogen and one or more of oxygen and nitrogen; and said $R^3$-$N^4$-sulfamethoxazole is water-soluble. $R^3$ is again preferably an amino acid or carbohydrate. Amino acids are preferred, for example tryptophan, tyrosine, histidine or tyrosine methyl ester have been specifically tested and found to function excellently or adequately. The linkage of $R^3$ is again preferably through the $N^4$ of the sulfamethoxazole and most preferably involves an azo linkage.

In one important aspect the present invention involves a composition of matter comprising $R^2$-($N^4$sulfonamide)$_n$. $R^2$ comprises carbon, hydrogen and one or more of oxygen and nitrogen; $R^2$ is bound to $N^4$ of $N^4$-sulfonamide. The number of sulfonamide, n, is greater than 1. Said $R^2$-($N^4$-sulfonamide is water-soluble to at least about 1 mg/ml. In the above formula, $R^2$ is preferably a synthetic polymer although it may be derived from natural sources if desired. Preferred synthetic polymers include amino acid homopolymers such as poly-L-tyrosine, for example. The number of sulfonamide ligands bound to $R^2$ is preferably greater than 1 and at least two. This number (n) is preferably 3, 4 or greater. While the preferred sulfonamide is sulfamethoxazole, others such as sulfamerazine, sulfanilic acid or sulfamethizole, for example are usable.

The present invention also involves a method for inhibiting allergic reactions of a subject to sulfonamides. The method comprises administering a therapeutically effective amount of $R^1N^4$-sulfonamide to the subject. $R^1$ is preferably bound to $N^4$ of sulfonamide and comprises carbon, hydrogen and one or more of oxygen and nitrogen. Said $R^1l$-$N^4l$-sulfonamide is water-soluble. Such allergic reactions are most preferably inhibited by use of monomeric $R^1$-$N^4$-sulfonamide derivatives. $R^1$ is again preferably an amino acid although it may be a carbohydrate or substitute such as imidazole. Preferred amino acids include histidine, tryptophan, tyrosine and tyrosine methyl ester. Although substituents analogous to amino acids such as imidazole may also be used, amino acids, being established natural substances, are preferred. The most significant characteristic of $R^1$ is that it ensures water solubility of the $R^1$-$N^4$ sulfanilamide. In the presence of an $R^1$-$N^4$-sulfonamide, the interaction between antibodies such as IgE specific for metabolically produced sulfonamide adducts and such adducts is inhibited, thus lessening various reactions such as the activation of mast cells and their production of histamine. The administration of $R^1N^4$ sulfonamide to a subject is preferably parenteral but may be enteral as well, given adequate absorption into the bloodstream. A preferred sulfonamide is again sulfamethoxazole although other drugs such as sulfamerazine, sulfanilic acid or sulfamethizole, for example may be used.

An important aspect of the present invention is a method for assessing the allergic status to sulfonamides of particular subjects. This method preferably comprises intradermally or percutaneously administering to a subject an effective amount of $R^2$-$(N^4$-sulfonamide$)_n$ and determining presence and size of any resultant wheal. $R^2$ preferably comprises carbon, hydrogen and one or more of oxygen and nitrogen and is preferably bound to an $N^4$ of $N^4$-sulfonamide. The number of sulfonamides bound, n, is greater than 1, said $R^2$-$(N^4$-sulfonamide$)_n$ being watersoluble to at least about 1 mg/ml. It is important that the number of sulfonamide units bound to $R^2$ is greater than 1, most preferably at least 2 and 3-4 being sufficient. It is also of importance that the $R^2$-$(N^4$sulfonamide$)_n$ is water-soluble to at least about 1 mg/ml. This allows adequate interdermal administration. A preferred $R^2$ is a synthetic polymer such as a polypeptide or polysaccharide. Preferred synthetic polypeptides are amino acid homopolymers such as poly-L-tyrosine, for example. The sulfonamide drug is again most preferably sulfamethoxazole although it may be any other sulfonamide drug such as sulfamerazine, sulfanilic acid or sulfamethizole.

For the inhibition of allergic reactions by the above described method, a preferred method comprises administering a therapeutically effective amount of $N^4$sulfamethoxazoyl-$R^3$ to a subject., $R^3$ comprises carbon, hydrogen, and one or more of oxygen and nitrogen, sufficient to render the $N^4$-sulfamethoxazoyl-$R^3$ water soluble. Analogous to those statements made earlier, $R^3$ is preferably an amino acid such as histidine, tyrosine, tryptophan or tyrosine methyl ester although it may also be a substituent such as imidazole or even a carbohydrate.

A particularly preferred compound usable in the assessment of allergic status to sulfonamide drugs is the compound $N^4$-sulfamethoxazoyl-poly-L-tyrosine comprising monomeric units having the configuration:

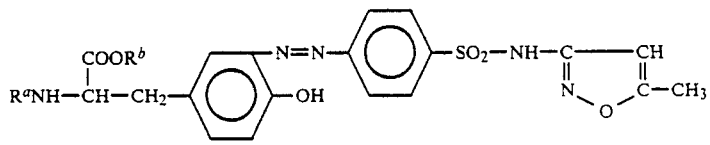

wherein $R^a$ and $R^b$ are additional $N^4$-sulfamethoxazoyl-L-tyrosine or L-tyrosine residues bound in amide linkage.

DESCRIPTION OF THE PREFERRED EMBODIMENTS

Allergic reactions to sulfonamide therapy occur in approximately 4% of normal patients and over 50% of HIV infected patients. These immunological reactions cause substantial morbidity. Such reactions preclude optimal therapy and prophylaxis in AIDS patients leading to use of expensive and often toxic. alternatives, increasing rates of hospitalization. Thus the direct and indirect costs of sulfonamide allergy are considerable. The present inventors have identified the principal hapten derived from sulfonamides and have synthesized univalent forms of the hapten that can block antibody binding to drug-carrier conjugates. These agents should be able to prevent or reverse allergic reactions to sulfonamides in vivo.

Prior to the inventor's work, the chemical form of sulfonamide-derived haptens was unknown. The present invention relates to assays for human IgG, IgA, IgM, and IgE, and many positive sera have been banked. Using these sera, fine specificity of antibodies to sulfonamides may be assessed. A variety of $N^4$-substitutions of sulfamethoxazole and other sulfonamides have been synthesized. Of the compounds studied to date, $N^4$-sulfamethoxazoyl histidine appears to be among the most active in inhibiting antibody binding to sulfamethoxazole-human serum albumin conjugates. Univalent hapten inhibition in humans has been shown to block penicillin-induced IgE-mediated reactions and to arrest serum sickness and hemolytic anemia. Univalent sulfonamide determinants should be able to prevent or stop antibody mediated reactions to sulfonamides. All of these assays and sulfonamide derived reagents are new and invented by the present applicant. No similar compounds have been previously reported. Univalent hapten inhibition would be particularly valuable in improving the care of AIDS patients while markedly reducing the cost of such care.

The present invention involves establishing assays for antibodies to sulfonamides. The prevalence of IgG, IgA, IgM, and IgE antibodies to sulfonamides such as SMX in the blood of control subjects, sulfonamide allergic patients, and randomly selected HIV+and AIDS patients is an aim of this invention. Univalent haptens have been prepared which are capable of inhibiting antibody binding to haptens of sulfonamides such as SMX on carrier molecules.

SMX was coupled to human serum albumin (HSA) or to histidine (HD) and a variety of other low MW molecules in the $N^4$-sulfonamidoyl configuration. SMX-HSA was used in radioallergoasorbent test (RAST) assays for IgE and ELISA assays for IgG, IgA, and IgM. Penicillin (penicilloyl) substituted HSA (P-HSA) was used in an IgG ELISA. Specificity was verified by demonstrating inhibition of binding with free SMX-HSA and SMX-HD (univalent hapten), but not with HSA or P-HSA.

In marked contrast to the high prevalence of Ig to SMX, only 3(6%) HIV+ and 0 AIDS patients expressed IgG to P-HSA. SMX-HD (! mM) added at the time of serum addition to ELISA plates inhibited Ig binding to the solid phase 34%-98%. (See Table 1). Other univalent haptens studied, and free SMX, also inhibited binding, but were usually less efficient.

Antibodies to SMX were detected in the majority of AIDS, HIV+, and SMX allergic patients. These data suggest an immunologic basis for many adverse reactions to SMX in AIDS patients. Hapten inhibition of Ig binding was shown to be feasible in vitro, making likely the possibility that hapten inhibition could be developed as a strategy to suppress clinical allergic reactions to SMX, analogous to previously developed system for allergy to penicillins (16).

TABLE 1

| Subjects | No. | Isotype Positive | | | | | (%) |
|---|---|---|---|---|---|---|---|
| | | IgG | IgA | IgM | IgE | Any+ | |
| Normal | 10 | 0 | 0 | 0 | 0 | 0 | (0%) |
| Allergic | 38 | 10 | 13 | 3 | 14 | 23 | (61%) |
| HIV+ | 51 | 47 | 13 | 20 | 4 | 48 | (94%) |
| AIDS | 17 | 12 | 6 | 4 | 2 | 15 | (88%) |

The following Examples are presented to exemplify important aspects of the present invention and are not meant to limit the scope of the invention unless otherwise specified in the pendant claims.

EXAMPLE 1

INHIBITION OF IgG BINDING

This experiment was performed to determine the amount of binding inhibition achieved with various inhibitory agents. The serum dilution at which binding inhibition was exhibited was also determined. The experiments were performed in 96-well microtiter plates having 8 rows designated A-H, and 12 columns designated 1-12. Each well of the microtiter plate was given a designation in accordance with the above grid system. All samples were diluted in phosphate buffered saline (PBS) to the designated dilution factor. The serum dilution levels used in this study were 1:40, 1:80 and 1:160, v/v.

A sample of each serum dilution was preincubated overnight with a IgG binding inhibitor selected from Table 2. A 2o-lambda (miorolitor) volume from a lo mg/ml solution of the selected inhibitor was added to a 180 lambda volume of the particular serum sample.

The following table (Table 2) denotes the numerical designations given each inhibitor used in the study.

TABLE 2

IgG BINDING INHIBITORS

| Numerical Designation | IgG Binding Inhibitor |
|---|---|
| 1 | SMX-Imidazole |
| 2 | SMX-Tryptophan |
| 3 | SMX-Tyrosine |
| 4 | SMX-Tyrosine Methyl ester |
| 5 | SMX-Lysine |
| 6 | SMX-HSA (Human Serum Albumin) |
| 7 | SMX-Polytyrosine |
| 8 | SMX-Histidine |
| 9 | Sulfamethoxazole-Histidine |
| 10 | Sulfamerazine-Histidine |
| 11 | Sulfanilic-Histidine |

One hundred milligrams (100 mg) of each of the listed compounds was weighed out and added to a 10 ml volume of 100% PBS so as to achieve a final concentration of 10 mg/ml by weight of the inhibitor.

In accordance with the aforedescribed system, the wells at Row A, columns 1 and 2 of the microtiter plate, received 100 microliters of phosphate buffered saline as a blank. Row A, columns 3 and 4, received normal serum diluted 1:40 in PBS, and served as a negative control. Row A, columns 5 and 6 received !00 microliters of a positive serum (i.e., serum sample positive for IgG to SMX) diluted !:40. Row A, columns 7 and 8, received positive serum diluted at 1:80. Similarly, Row A, columns 9 and 10, received 100 microliters positive serum diluted at 1:160. Beginning with Row A, columns 11 and 12, all wells received a 100 microliter volume of positive serum that had been preincubated overnight with one of the potential inhibitors described in Table 2 (#1-11). The completed microtiter plate consisted of the following sample distribution (see Table 3).

TABLE 3

MICROTITER PLATE TEST GRID

| | 1 | 2 | 3 | 4 | 5 | 6 | 7 | 8 | 9 | 10 | 11 | 12 |
|---|---|---|---|---|---|---|---|---|---|---|---|---|
| A | PBS | PBS | NS 1:40 | NS 1:40 | +S 1:40 | +S 1:40 | +S 1:80 | +S 1:80 | +S 1:160 | +S 1:160 | 1 A | 1 A |
| B | 1 B | 1 B | 1 C | 1 C | 2 A | 2 A | 2 B | 2 B | 2 C | 2 C | 3 A | 3 A |
| C | 3 B | 3 B | 3 C | 3 C | 4 A | 4 A | 4 B | 4 B | 4 C | 4 C | 5 A | 5 A |
| D | 5 B | 5 B | 5 C | 5 C | 6 A | 6 A | 6 B | 6 B | 6 C | 6 C | 7 A | 7 A |
| E | 7 B | 7 B | 7 C | 7 C | 8 A | 8 A | 8 B | 8 B | 8 C | 8 C | 9 A | 9 A |
| F | 9 B | 9 B | 9 C | 9 C | 10 A | 10 A | 10 B | 10 B | 10 C | 10 C | 11 A | 11 A |
| G | 11 | 11 | 11 | 11 | | | | | | | | |

TABLE 3-continued

| MICROTITER PLATE TEST GRID | | | | | | | | | | | |
|---|---|---|---|---|---|---|---|---|---|---|---|
| 1 | 2 | 3 | 4 | 5 | 6 | 7 | 8 | 9 | 10 | 11 | 12 |
| B | B | C | C | | | | | | | | |

Table Legend:
*NS = Normal Serum
*+S = Serum Sample ⊕ for IgG to SMX
*1-11 = Preincubation binding inhibitor
*A = + Serum diluted 1:40
B = + Serum diluted 1:80
C = + Serum diluted 1:160

The uninhibited binding was 1:40, Row A, columns 5 and 6; 1:80, Row A, column 7 and 8; 1:160, Row C, column 9 and 10. Percent inhibition of binding was calculated on the basis of decrease in Optical Density (O.D.). The percent inhibition of each inhibitor at the various serum diolutions is summarized in Table 4.

TABLE 4

| REDUCTION IN PERCENT BINDING | | | | |
|---|---|---|---|---|
| | | Dilution | | |
| | | 1:40 | 1:80 | 1:160 |
| Inhibitor | 1 | 8% | 12% | 23% |
| (from Table 2) | 2 | 0% | 1% | 0% |
| | *3 | 28% | 50% | 42% |
| | 4 | 22% | 6% | 8% |
| | 5 | 0% | 16% | 0% |
| | 6 | 10% | 9% | 0% |
| | *7 | 32% | 39% | 0% |
| | 8 | 3% | 1% | 0% |
| | *0 | 0% | 25% | 23% |
| | 10 | 0% | 0% | 0% |
| | 11 | 0% | 3% | 59%* |
| Control-0 | 12 | 100 | 100% | 100% |

*denotes statistically significant reduction in percent binding from controls.

These results indicate the SMX- tyrosine (#3) and SMX- poly-tyrosine (#7) significantly inhibit binding. SMX- tyrosine methyl ester (#4) produced considerable inhibition at the 1:40 serum dilution only. SMX-Histidine elicited significant reduction in binding at the 1:80 and 1:160 serum dilution, but none at the 1:40 dilution.

EXAMPLE 2

HAPTEN INHIBITION

This experiment was performed to examine percent inhibition of IgG binding using a final serum dilution of 1:80. This concentration was chosen to correct for the level of nonspecific binding see in Example 1.

The assay was set up using a 96 well microtiter plate. None of the serum samples were preincubated with inhibitor. Serum used was positive (+) for IgG to SMX, and was used at a final dilution of 180 for all wells.

A variety of binding inhibitors were employed at varying concentrations. The numerical designations given the inhibitor and/or the particular dilutions of the given inhibitor are listed in Table 5. A 10 mg/ml solution of each of the inhibitors was prepared as outlined in Example 1.

TABLE 5

| BINDING INHIBITORS | |
|---|---|
| Numerical Designation | Inhibitor |
| 1 | SMX-Tyrosine |
| 2 | SMX-Tyrosine methyl ester |
| 3 | SMX-poly-L-tyrosine |
| 4 | SMX -Histidine |
| 5 | SMX-Imidazole |
| 6 | SMX-Lysine |
| 7 | SMX-Tryptophan |
| 8 | SMX-HSA |
| 9 | Sulfamethizole-histidine |
| 10 | Sulfamerazine-histidine |
| 11 | Sulfanilic-histidine |
| 12 | SMX-HSA 3 mg/ml |
| 13 | SMX-HSA 1 mg/ml |
| 14 | SMX-HSA 0.3 mg/ml |
| 15 | SMX-HSA 0.1 mg/ml |
| 16 | SMX-Tyrosine 3 mg/ml |
| 17 | SMX-Tyrosine 1 mg/ml |
| 18 | SMX-Tyrosine 0.3 mg/ml |
| 19 | SMX-Tyrosine 0.1 mg/ml |
| 20 | SMX-poly-L-tyrosine 3 mg/ml |
| 21 | SMX-poly-L-tyrosine 1 mg/ml |
| 22 | SMX-poly-L-tyrosine 0.3 mg/ml |
| 23 | SMX-poly-L-tyrosine 0.1 mg/ml |

A 50 microliter volume of each numerically designated inhibitor was added each well of the plate. A 50 microliter volume of serum (1:40 dilution) positive to IgG to SMX was then added to each well. The final dilution of serum in each was then 1:80. The wells in the plate had the following sample distribution shown in Table 6.

TABLE 6

| MICROTITER PLATE SAMPLE DISTRIBUTION | | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| A | PBS | PBS | PBS | PBS | 1 | 1 | 2 | 2 | 3 | 3 | 4 | 4 |
| | | | NS | NS | +S | +S | +S | +S | +S | +S | +S | +S |
| B | 5 | 5 | 6 | 6 | 7 | 7 | 8 | 8 | 9 | 9 | 10 | 10 |
| | +S | +S | +S | +S | +S | +S | +S | +S | +S | +S | +S | +S |
| C | 11 | 11 | 12 | 12 | 13 | 13 | 14 | 14 | 15 | 15 | 16 | 16 |
| | +S | +S | +S | +S | +S | +S | +S | +S | +S | +S | +S | +S |
| D | 17 | 17 | 18 | 18 | 19 | 19 | 20 | 20 | 21 | 21 | 22 | 22 |
| | +S | +S | +S | +S | +S | +S | +S | +S | +S | +S | +S | +S |
| E | 23 | 23 | | | | | | | | | | |
| | +S | +S | | | | | | | | | | |

NS = Normal serum
+S = serum sample positive for IgG to SMX
1-13 = Binding Inhibitor The microtiter plate was then shaken slightly to mix the contents of each well and then the standard ELISA assay was performed. The plate was then allowed to incubate for 2 hours at room temperature. The plates were then washed and the OD readings taken for each well.

Percent inhibition was then calculated for each sample on the basis of decrease in OD. The percent inhibition obtained for each sample is summarized at Table 7.

TABLE 7
PERCENT INHIBITION

| | Inhibitor | Concentration | % Inhibition |
|---|---|---|---|
| 1 | SMX-Tyrosine | 10 mg/ml | 59 |
| 2 | SMX-Tyrosine | 3 mg/ml | 70 |
| 3 | SMX-Tyrosine | 1 mg/ml | 57 |
| 4 | SMX-Tyrosine | 0.3 mg/ml | 54 |
| 5 | SMX-Tyrosine | 0.1 mg/ml | 51 |
| 6 | SMX-Tyrosine Methyl ester | 10 mg/ml | 32 |
| 7 | SMX-poly-L-tyrosine | 10 mg/ml | 50 |
| 8 | SMX-poly-L-tyrosine | 3 mg/ml | 46 |
| 9 | SMX-poly-L-tyrosine | 1 mg/ml | 24 |
| 10 | SMX-poly-L-tyrosine | 0.3 mg/ml | 2 |
| 11 | SMX-poly-L-tyrosine | 0.1 mg/ml | 0 |
| 12 | SMX-Histidine | 10 mg/ml | 54 |
| 13 | SMX-Imidazole | 10 mg/ml | 61 |
| 14 | SMX-Lysine | 10 mg/ml | 51 |
| 15 | SMX-Tryptophan | 10 mg/ml | 52 |
| 16 | SMX-HSA | 10 mg/ml | 59 |
| 17 | SMX-HSA | 3 mg/ml | 55 |
| 18 | SMX-HSA | 1 mg/ml | 54 |
| 19 | SMX-HSA | 0.3 mg/ml | 54 |
| 20 | SMX-HSA | 0.1 mg/ml | 53 |
| 21 | Sulfamethazole-histidine | 10 mg/ml | 7 |
| 22 | Sulfamerazine-histidine | 10 mg/ml | 35 |
| 23 | Sulfanilic-histidine | 10 mg/ml | 60 |
| 24 | PBS | | 0 |
| 25 | TOTAL | | — |

EXAMPLE 3

INHIBITION STUDIES

This study was conducted to confirm results on binding inhibition obtained in Example 2. Two positive serums (i.e., positive for IgG to SMX) were employed, including the positive serum used in Examples 1 and 2. PBS (phosphate buffered saline) and a normal serum were also tested in this study.

All serum used were at a 1:40 final dilution. Serum was diluted in PBS.

Several binding inhibitors at various dilutions were used. The particular inhibitors and the dilutions thereof examined appear in Table 8, along with their numerical designations.

TABLE 8
BINDING INHIBITORS

| | Inhibitor | Concentration |
|---|---|---|
| 1. | SMX-TYR (Tyrosine) | 10 mg/ml |
| 2. | SMX-TYR (Tyrosine) | 1 mg/ml |
| 3. | SMX-TYR (Tyrosine) | 0.1 mg/ml |
| 4. | SMX-TYR (Tyrosine) | 0.01 mg/ml |
| 5. | SMX-TYR (Tyrosine) | 0.001 mg/ml |
| 6. | SMX-poly-L-TYR (Tyrosine) | 10 mg/ml |
| 7. | SMX-poly-L-TYR (Tyrosine) | 3 mg/ml |
| 8. | SMX-poly-L-TYR (Tyrosine) | 1 mg/ml |
| 9. | SMX-poly-L-TYR (Tyrosine) | 0.3 mg/ml |
| 10. | SMX-HSA | 10 mg/ml |
| 11. | SMX-HSA | 1 mg/ml |
| 12. | SMX-HSA | 0.1 mg/ml |
| 13. | SMX-HSA | 0.01 mg/ml |
| 14. | SMX-HSA | 0.001 mg/ml |
| 15. | SMX-HD | 10 mg/ml |
| 16. | SMX-HD | 1 mg/ml |
| 17. | SMX-HD | 0.1 mg/ml |
| 18. | SMX-HD | 0.01 mg/ml |
| 19. | SMX-HD | 0.001 mg/ml |
| 20. | Sulfamerazine-HD | 10 mg/ml |
| 21. | Sulfamethizole-HD | 10 mg/ml |
| 22. | Sulfanilic-HD | 10 mg/ml |
| 23. | Sulfanilic-HD | 3 mg/ml |
| 24. | Sulfanilic-HD | 1 mg/ml |
| 25. | Sulfanilic-HD | 0.3 mg/ml |
| 26. | Sulfanilic-HD | 0.1 mg/ml |
| 27. | HSA alone | 10 mg/ml |
| 28. | BPO-BA (penicilloyl-benzylamine) | 10 mg/ml |
| 29. | BPO-HSA (penicilloyl-HSA) | 10 mg/ml |

Positive serum samples were first preincubated overnight with 50 microliter of the numerically designated inhibitors (10 mg/ml inhibitor solution - See Example I).

A standard ELISA assay was conducted using a 96 well microtiter plate as described for Example I. Row A, wells 3 and 4, received normal serum diluted 1:40 in PBS. Other wells received 10 microliter of positive serum A (Row A, well 5 through Row F, well 6) or positive serum B (Row F, well 7 through Row H, well 6) at a 1:40 dilution in PBS.

The microtiter test plate was prepared according to the above scheme and appears in Table 9.

TABLE 9
MICROTITER PLATE WELL DISTRIBUTION

| | 1 | 2 | 3 | 4 | 5 | 6 | 7 | 8 | 9 | 10 | 11 | 12 |
|---|---|---|---|---|---|---|---|---|---|---|---|---|
| A | PBS | PBS | PBS NS | PBS NS | PBS A+ | PBS A+ | 1 A+ | 1 A+ | 2 A+ | 2 A+ | 3 A+ | 3 A+ |
| B | 4 A+ | 4 A+ | 5 A+ | 5 A+ | 6 A+ | 6 A+ | 7 A+ | 7 A+ | 8 A+ | 8 A+ | 9 A+ | 9 A+ |
| C | 10 A+ | 10 A+ | 11 A+ | 11 A+ | 12 A+ | 12 A+ | 13 A+ | 13 A+ | 14 A+ | 14 A+ | 15 A+ | 15 A+ |
| D | 16 A+ | 16 A+ | 17 A+ | 17 A+ | 18 A+ | 18 A+ | 19 A+ | 19 A+ | 20 A+ | 20 A+ | 21 A+ | 21 A+ |
| E | 22 A+ | 22 A+ | 23 A+ | 23 A+ | 24 A+ | 24 A+ | 25 A+ | 25 A+ | 26 A+ | 26 A+ | 27 A+ | 27 A+ |
| F | 28 A+ | 28 A+ | 29 A+ | 29 A+ | PBS A+ | PBS A+ | PBS B+ | PBS B+ | 1 B+ | 1 B+ | 6 B+ | 6 B+ |
| G | 10 B+ | 10 B+ | 15 B+ | 15 B+ | 20 B+ | 20 B+ | 21 B+ | 21 B+ | 22 B+ | 22 B+ | 27 B+ | 27 B+ |
| H | 28 B+ | 28 B+ | 29 B+ | 29 B+ | PBS B+ | PBS B+ | | | | | | |

That percent binding inhibition obtained for each sample appears at Table 10.

TABLE 10
PERCENT REDUCTION IN BINDING

| Binding Inhibitor | % Reduction in OD |
|---|---|
| 1 | 37 |
| 2 | 18 |

TABLE 10-continued

PERCENT REDUCTION IN BINDING

| Binding Inhibitor | % Reduction in OD |
| --- | --- |
| 3 | 32 |
| 4 | 15 |
| 5 | 4 |
| 6 | 41 |
| 7 | 47 |
| 8 | 34 |
| 9 | 3 |
| 10 | 56 |
| 11 | 34 |
| 12 | 12 |
| 13 | 17 |
| 14 | 5 |
| 15 | 17 |
| 16 | 10 |
| 17 | 4 |
| 18 | 3 |
| 19 | 6 |
| 20 | 8 |
| 21 | 0 |
| 22 | 75 |
| 23 | 0 |
| 24 | 0 |
| 25 | 0 |
| 26 | 0 |
| 27 | 0 |
| 28 | 0 |
| 29 PBS | 0 |

This data indicates a concentration dependence in addition to antibody binding.

EXAMPLE 4

PATIENT ANTIBODY STUDIES

Patient antibody studies were performed on the blood of normal control subjects, SMX-allergic patients and randomly selected HIV and AIDS patients. A total of 53 samples from different subjects were tested. SMX was coupled to human serum albumin (HSA) or to histidine (HD) and a variety of other low MW molecules in the $N^4$-sulfonamidoyl configuration. SMX-HSA was used in a radioallergosorbent (RAST) assay for IgE and ELISA assays for IgG, IgA, and IgM. Penicillin (penicilloyl) substituted HSA (P-HSA) was used in an IgG ELISA. Specificity was verified by demonstrating inhibition of binding with free SMX-HSA and SMX-HD (univalent hapten), but not with HSA or P-HSA. The results from these studies are shown in Table 11.

TABLE 11

ANTIBODY STUDIES IN HIV INFECTED PATIENTS

|  | HIV & AIDS | PRE-AIDS HIV INFECTED |
| --- | --- | --- |
| Patient Distribution | 17 | 51 |
| History of sulfa allergy | 29%*** | 4% |
| IgG to SMX | 76% | 90% |
| IgA to SMX | 36% | 24% |
| IgM to SMX | 24% | 39% |
| IgE to SMX | 0% | 12% |
| *anti BPO | 0 | 2% |
| *anti BPE | 0 | 6% |

*BPO = benzylpenicilloyl determinant
*BPE = benzylpenicillenyl determinant
***percent total having antibodies When the same test was used for penicillin determinants, no antibodies were found.

EXAMPLE 5

ISOTYPE SPECIFIC ELISA

The present invention was tested using a modified ELISA assay. The specific ELISA used employs the following reagents, standards and antibodies.

Reagents:
  Borax (Sodium tetraborate 10 $H_{20}$) —Sigma Cat. #B-9876
  Boric Acid —Sigma Cat. *B-0252
  Saline—1 liter bottles from General Hospital Stores
  Sodium Phosphate —Monobasic ($NaH_2PO_4$) - Sigma Cat. #S-0751
  Sodium Phosphate —Dibasic ($Na_2HPO_4$) - Sigma Cat. #S-0876
  Tween 20 (polyoxyethelene [20]sorbitan monolaurate) —Sigma Cat. #P-1379
  ELISA Plates —Scientific Products Dynatech Laboratories Plate Sealing Tape 66 mm —Titertek Flow Lab 77-420-00 OPD (o-Phenylenediamine Dihydrochloride light sensitive) —Sigma Cat., #PP-3888
  30% $H_2O_2$ —Fisher Scientific #H-325
  6 M $H_2SO_4$ Standards: Human IgA —Calbiochem-Behring Corp., LaJolla, CA 92037 —Cat. #BB1802
  Human IgG —Calbiochem-Behring Corp., Cat. #BB1807
  Human IgM —Purified Kappa, Tago, Inc., Burlingame, CA 94010

Antibodies:
  Affinity purified goat anti-human —Tago, Inc.
    —IgA 4101
    —IgG 4100
    —IgM 4102
  15 Peroxidase conjugated antibodies —Tago, Inc.
    —IgA 2391
    —IgG 2390
    —IgM 2392

Buffers:
  1. Coating Buffer
    0.125M Borate Buffered Saline pH 8.2.
      Add 6.184 gm Boric Acid and 9.536 gm Borax to 1 Liter Saline.
      Adjust pH to 8.2 with HCl.
  2. Tween PBS
    —To make 0.05M PBS pH 7.1:
      28 ml of solution A (0.5M $NaH_2PO_4$) and 72 ml of solution B (0.5M $Na_2HPO_4$) and 37.5 ml 4M NaCl.
      Adjust to final volume of 1 Liter.
      Add 0.5 ml Tween 20 to 1 Liter PBS.
  3. ELISA WASH - Tween Saline
    —To 10 L water:
      Add 5 ml Tween 20 and 85 gm NaCl.
  4. Substrate Solution
    —Must be made fresh just before developing plate
      To 99 mls of water, add 0.015ml of 30% $HO_2$. 1 mg 1 ml OPD.
      Weigh out 10 mgs of OPD and dissolve in 1 ml of absolute methanol.
      Add to water $H_2O_2$ mixture.

The specific procedure employed includes the following steps:
To coat plates:
  Dilute unconjugated antibody in Borate Buffered Saline. Appropriate dilution is dependent on the antibody used and needs to be determined as below (10 ml of coating solution per plate):
    Add 0.1 ml to wells leaving column 1 empty for no coat control.
    Label plate with antibody (red for anti-IgA, blue for anti-IgG, and black for anti-IgM) and date.
    Seal with plate sealing tape.
    Incubate at 37° C. overnight.
    Refrigerate.
    Plates may be stored for a month.
To determine the optimal coating concentration:
    Plates will be coated as above with the following:
        Column 1 —no coat.
        Columns 2 and 3 —optimal concentration of previous antibody.
        Columns 4 thru 12 —with serial dilutions of the material to be tested. Generally the optimal coating concentration will be around 5 microgram of protein per ml. For Tago Affinity purified antibodies, the optimal dilution will be approximately 1/500; so you would test at 1/750, 1/500, 1/400, 1/300, and 1/200 dilutions
    After coating, use the isotype specific standard, diluting serially down the plate -2-fold dilutions, leav row H without standard.
    Incubate with isotype specific HRP conjugate and develop. Use the concentration with the largest dilution that gives the greatest range.
ELISA ASSAY:
1. Coat plates as above.
2. Wash plate 8 times with Tween Saline. (4x)
3. Add 0.1ml of Tween PBS to each well.
4. To columns 1–3, add 0.1 ml of isotype specific standard diluted in Tween PBS
    –For IgM add 2000 ng/ml.
    –For IgA and IgG, add 1000 ng/ml.
5. To columns 4–11, add 0.1 ml of culture supernatant or other test samples
    16 samples may be done if samples are put in Rows A and E.
6. Make serial 2-fold dilutions of standards and samples by mixing and taking .1 ml from Row A and putting it into Row B, mixing and removing 0.1 ml. The standards are diluted to Row G, and 0.1 ml are removed and discarded. Row H gets no standard or sample in columns 1–3; it is the control for non-specific binding of conjugate to coat.
The samples are diluted 3 times. 7. Cover and incubate at 37° C. for 2 hours.
8. Wash plate with Tween Saline 8 times.
9. Dilute isotype specific HRP conjugate in Tween-PBS. For Tago Affinity purified conjugates, it is usually a 1/1000dilution.
10. Add 0.1 ml per well, all wells (11 ml/plate).
11. Cover and incubate for 2 hours at 37° C.
12. Make developing solution.
13. Wash plate 8 times with Tween Saline.
14. Add 0.1 ml of developing solution to all wells.
15. Development is linear so that standard can be stopped at 2 minutes and samples can go 4 minutes and the results will be divided by 2. However, it is best to stop the whole plate at once and all the plates with the same coat to be compared after the same length of time (i.e., all IgA plates at 3 minutes, all IgM plates at 5 minutes).
16. Stop Enzyme reaction with 0.050 ml 6M $H_2SO_4$.
17. Read at 492 absorbance on automated ELISA reader.

To calculate Immunoglobulin in ngs/ml
    –Using 3–4 cycle logarithmic paper, draw standard curve.
    –Horizontal axis will be dilution of standard.
    For example, IgG and IgA - 500 ng/ml, 250, 125, 62.5, 31.2, 15.6, 7.8. IgM starts at 1000 ng/ml and goes to 15.6 ng/ml.
    –The vertical axis is the absorbance at 492.
    –Find the absorbance of the sample and find the area on the standard curve that it touches. Read the ng 1 ml off the horizontal axis =ng/ml in well. Then multiply by the dilution of the sample (Example: A sample from Row A =1:2 dilution, so multiply by 2; if from Row B =1:4 dilution, so multiply by 4). If samples were stopped at 4 minutes and standards at two minutes, find the ng/ml in sample and divide by 2.

EXAMPLE 6

PREPARATION OF SULFAMETHOXAZOLE (SMX)-HSA

The sulfamethoxazole (SMX)-HSA, reagent used in the present invention was prepared according to the following procedure. First, the diazonium salt of SMX was prepared with the following reagents in the procedure outlined below.
REAGENTS:
    Sulfamethoxazole (MW 253): 80 mg(0.316 moles)
    HCl (1 N(: 4 ml
    Sodium nitrite (FW 69): 60 mg
    Distilled water: 10 m
PROCEDURE:
1. Dissolve 80 mg of SMX in 4 mL of 1 N HCl in a 15 ml tube.
2. Place tube in an ice water-filled small beaker.
3. Dissolve sodium nitrate in water at 14 mg/mL: take 2.90 mL and place in a tube: chill in an ice water bath.
4. Add sodium nitrite to SMX dropwise as follows:
    A. Add 1 drop of sodium nitrite; Vortex.
    B. Chill in ice bath for 30 seconds.
    C. Repeat until 2.90 ml of sodium nitrite added.
    D. Keep on ice.
5. Use immediately for conjugation to protein.

The prepared SMX salt was then conjugated to the protein using the following described reagents in the procedure outline below.
REAGENTS:

| Buffer: | Sodium chloride | 7.6 mg/mL (0.13 M) |
| --- | --- | --- |
| | Boric acid | 9.9 mg/mL (0.16 M) |

NaOH (0.5M)
Human serum albumin (HSA) .... 500 mg
Diazonium salt of SMX prepared as above.
PROCEDURE:
1. Dissolve 500 mg of HSA in 20 mL of buffer & adjust pH to 9.0.
2. Place in a beaker in an ice bath, with a stirring bar and pH probe.
3. Add diazonium salt of SMX dropwise. Keep pH at 9.0–9.5 with NaOH.
4. Stir for 60 minutes in ice bath, after the last addition.
5. Dialyze vs PBS x 2, then vs water x 2.

6. Measure OD$_{359}$ of dialyzed conjugate 1:10 in PBS vs 1.86 mg/mL HSA in PBS. Dilute both if needed to get on scale.

7. Lyophilize.

Derivatives produced by reacting diazotized sulfamethoxazole with amino acids were routinely purified by a thin layer of chromatography. A silica plate was used and a solvent of 70% methanol: 30% water. It was noted in these purifications that the diazotized SMX amino acid derivatives characteristically were deeply colored (most frequently orange). The SMX itself had a Rf of 0.25 and SMX-HD had an Rf of 0.70. The colored SMX derivatives were removed from the plate as purified. SMX derivatives of, for example tyrosine and polytyrosine, were found to have a peek absorption at about 306 nanometers. Utilizing this absorption maximum and calculated absorption values, the substitution of poly-L-tyrosine used in the determinations described herein was found to be 189 SMX per molecule of poly-L-tyrosine.

EXAMPLE 7

PREPARATION OF SULFAMETHOXAZOLE (SMX)-HISTIDINE

The sulfamethoxazole (SMX)-Histidine reagent used in the present invention was prepared according to the following procedure. First, the diazonium salt of SMX was prepared with the following reagents in the procedure outlined below.

REAGENTS:
Sulfamethoxazole (MW 253): 40 mg
HCl (1 N): 2 ml
Sodium nitrite (FW 69): 60 mg
Distilled water: 10 ml PROCEDURE:
Dissolve 40 mg of SMX in 2 ml of 1 N HCl in a 15 ml tube.
2. Place tube in ice water-filled small beaker.
3. Dissolve sodium nitrite in water at 14 mg/ml: take 1.45 ml and place in a tube: chill in ice water bath.
4. Add sodium nitrite to SMX dropwise as follows:
   A. Add 1 drop of sodium nitrite; Vortex.
   B. Chill in ice bath for 30 seconds.
   C. Repeat until 1.45 ml of sodium nitrite added.
   D. Keep on ice.
5. Use immediately for conjugation to protein.

The prepared SMX salt was then conjugated to the protein using the following described reagents in the procedure outlined below.

REAGENTS:
Histidine (HD) .... 245 mg
Diazonium salt of SMX prepared above.

PROCEDURE:
1. Dissolve 245 mg histidine in 10 ml of buffer and adjust pH to 9.0.
2. Place in a beaker in an ice bath, with a stirring bar and a pH probe.
3. Add diazonium salt of SMX dropwise. Keep pH at 9.0–9.5 with NaOH.
4. Stir for 60 minutes in ice bath, after the last addition.
5. Dialyze vs PBS x 2, then vs water x 2.
6. Measure OD at 250–450 of dialyzed conjugate at every 10 nm. (20 nm, 260 nm, 270, etc.).

EXAMPLE 8

PREPARATION OF SULFAMETHOOXAZOLE (SMX) - SULFA CONJUGATES

The sulfamethoxazole (SMX) - sulfa conjugates reagents used in the present invention was prepared according to the following procedure.

1. Weigh out the following:
   a. Sulfanilic acid: 27 mg
   b. Sulfamethizole: 43 mg
   c. Sulfamerazine: 42 mg
2. Process each of elements a-c individually as follows:
   a. Dissolve in 2 ml 1N HCl in a 15 ml tube.
   b. Place tube in an ice water filled small beaker.
   c. Dissolve sodium nitrite in water at 14 mg/ml: take 1.45 ml and place in a tube: chill in an ice water bath.
   d. Add sodium nitrite dropwise. Vortex, chill in ice bath for 30 seconds. Repeat until 1.45 ml of sodium nitrite is added.
   e. Keep on ice.
3. Dissolve 245 mg histidine in 10 ml borate buffer (see Example VI).
4. Place in a beaker in an ice bath, with a stirring bar and a pH probe.
5. Add sulfa compound dropwise keeping the pH at between 9.0–9.5 with NaOH.
6. Stir 60 minutes after last drop is added.
7. Correct pH to about 7.4
8 Lyophilize The literature citations in the following list are incorporated in pertinent part by reference herein for the reasons cited in the text.

REFERENCES

1. Lawson DH. Adverse effects of cotrimoxazole. In: Hitchings GH, ed. Inhibition of folate metabolism in chemotherapy. New York: Springer-Verlag. 1983; 207-28.
2. Sullivan TJ. Allergic reactions to antimicrobial agents: a review of reactions to drugs not in the beta lactam antibiotic class. J. Allergy Clin. Immunol. 1984; 74:594.
3. Arndt KA., Jick H. Rates of cutaneous reactions to drugs. JAMA 1976; 235:918.
4. Miller KD., Lobel HO., Satriale RF., et al. Severe cutaneous reactions among American travelers using pyrimethamine-sulfadoxine (Fansidar) for malaria prophylaxis. Am. J. Trop. Med. Hyg. 1986; 35:451.
5. Hjorth N., Fregert S., Contact dermatitis. In: Rook A., Wilkinson DA., Ebling FJG., eds. Textbook of dermatology, vol. 1. Philadelphia: FA Davis. 1968; 255-62.
6. Baer RL., Harber LC. Reactions to light, heat, and trauma. In: Samter M., ed. Immunologic diseases. Boston: Little Brown, 1971; 973-8.
5 7. Ratner B. Allergy from sulfonamide therapy. In: Ratner B. ed. Allergy, anaphylaxis, and immunotherapy. Baltimore: Williams & Wilkins, 1943; 579-89.
8. Parker CW. Drug allergy. In: Parker CW, ed. Clinical immunology. Philadelphia: 1980, WB Saunders, 1980; 1219-60.
9 Wormser GP., Keusch GT. Trim®thoprimsulfamethoxazole in the United States. Ann. intern. Med. 1979; 91:420.

10. Sherman WB., Cooke RA. Sulfadiazine sensitivity with demonstrable skin-sensitizing antibody in the serum. Am. J. Med. 1947; 2:588.

11. Mayer RL. Group sensitization to compounds of quinone structure and its biochemical basis: role of these substances in cancer. Prog. Allergy 1964; 4:79.

12. Sulzberger MB., Kanof A., Baer RL., Lowenberg C. Sensitization by topical application of sulfonamides. J. Allergy 1947; 18:92.

13. Sarkany I. Lymphocyte transformation in drug hypersensitivity. Lancet 1967; 1:743.

14. Warrington RJ., Sauder PJ., McPhillips S. Lymphocyte transformation studies in suspected hypersensitivity to trimethoprim-sulfamethoxazole. Clin Allergy 1983; 13:235.

15. Carrington, DM., Earl HS., and Sullivan TJ. Studies of Human IgE to a Sulfonamide Determinant. J. Allergy and Clin. Immunol., 1987; 79:442.

16. deWeck, AL. and Girard, JP. Specific Inhibition of Allergic Reactions to Penicillin in Man by a Monovalent Hapten. Int. Arch. Allergy, 1972; 42:798.

Changes may be made in the components such as sulfonamides and ligands bound thereto described herein or in the steps or the sequence of steps of the methods described herein without departing from the concept and scope of the invention as defined in the following claims.

What is claimed is:

1. A method for inhibiting allergic reactions to an antibiotic sulfanilamide, the method comprising administering a therapeutically effective amount of an $R^1$-$N^4$-sulfanilamide wherein $R^1$ is bound through an azo linkage to an antibiotic sulfanilamide;

$R^1$ is a radical of an amino acid, amino acid a polymer or imidazole; and said $R^1$-$N^4$-sulfanilamide is water-soluble.

2. The method of claim 1 wherein $R^1$ is an amino acid radical.

3. The method of claim 1 wherein $R^1$ is a radical of tryptophan, histidine, lysine, imidazole, tyrosine, or tyrosine methyl ester.

4. The method of claim 1 wherein the administering is parenteral.

5. The method of claim 1 wherein the administering is enteral.

6. The method of claim 1 wherein the antibiotic sulfanilamide is sulfamethoxazole.

7. The method of claim 1 wherein the antibiotic sulfanilamide is sulfamerazine, sulfanilic acid or sulfamethizole.

8. A method for assessing an allergic status of a patient to ann antibiotic sulfanilamide, the method comprising intradermally or percutaneously administering to said patient suspected of being allergic to an antibiotic sulfanilamide ann effective amount of $R^2$-$(N^4$-sulfanilamide$)_n$ and determining presence and size of any resulting wheal, wherein:

$R^2$ is a radical of an amino acid polymer;

$R^2$ is bound through an azo linkage to an antibiotic sulfanilamide; and n is greater than 1;

said $R^2$-$(N^4$-sulfanilamide$)_n$ being water-soluble to at least 1 mg/ml.

9. The method of claim 8 wherein $R^2$ is a synthetic amino acid polymer.

10. The method of claim 8 wherein $R^2$ is a polypeptide.

11. The method of claim 8 wherein $R^2$ is an amino acid homopolymer.

12. The method of claim 8 wherein $R^2$ is poly-L-tyrosine.

13. The method of claim 8 wherein n is 2.

14. The method of claim 8 wherein n is 3 or 4.

15. The method of claim 8 wherein the sulfanilamide is sulfamethoxazole.

16. The method of claim 8 wherein the sulfanilamide is sulfamerazine, sulfanilic acid or sulfamethizole.

17. A method for inhibiting allergic reactions of a subject to an antibiotic sulfanilamide, the method comprising administering a therapeutically effective amount of $R^3$-$N^4$-sulfamethoxazole to a subject, wherein $R^3$ is bound through an azo linkage, and is a radical of an amino acid, amino acid polymer or imidazole, said $R^3$-$N^4$-sulfamethoxazole being water-soluble.

18. The method of claim 17 wherein $R^3$ is an amino acid.

19. The method of claim 17 wherein $R^3$ is histidine.

20. The method of claim 19 wherein $R^3$ is tyrosine.

21. The method of claim 17 wherein $R^3$ is imidazole.

22. A method for inhibiting allergic reactions of a subject to an antibiotic sulfanilamide, the method comprising administering a therapeutically effective amount of $N^4$-sulfamethoxyazoyl-L-histidine.

23. A method for inhibiting allergic reactions of a subject to an antibiotic sulfanilamide, the method comprising administering a therapeutically effective amount of $N^4$-sulfamethoxazoyl-L-tyrosine.

24. A method for inhibiting allergic reactions of a subject to an antibiotic sulfanilamide, the method comprising administering a therapeutically effective amount of $N^4$-sulfamethoxyazoyl-L-tyrosine.

25. A method for inhibiting allergic reactions of a subject to an antibiotic sulfanilamide, the method comprising administering a therapeutically effective amount of $N^4$-sulfamethoxyazoyl-poly L-tyrosine.

26. The method of claim 17, 22 or 23 wherein the subject is defined further as being already allergic to an antibiotic sulfanilamide.

27. The method of claim 17, 22 or 23 wherein the therapeutically effective amount is between 0.3 mg/kg and 30 mg/kg body weight.

* * * * *

UNITED STATES PATENT AND TRADEMARK OFFICE
CERTIFICATE OF CORRECTION

PATENT NO.   :   5,064,637

DATED        :   November 12, 1991

INVENTOR(S)  :   Timothy J. Sullivan

It is certified that error appears in the above-identified patent and that said Letters Patent is hereby corrected as shown below:

In claim 1, column 17, line 35 delete the word "a" between the words 'acid' and 'polymer'.

In claim 8, column 17, line 54 delete the term "ann" and insert the word --an-- therefor.

In claim 8, column 17, line 57 delete the term "ann" and insert the word --an-- therefor.

In claim 20, column 18, line 33, delete the number "19" and insert the number --17-- therefor.

Signed and Sealed this

Sixteenth Day of February, 1993

Attest:

STEPHEN G. KUNIN

*Attesting Officer*         *Acting Commissioner of Patents and Trademarks*